United States Patent [19]

Toon et al.

[11] Patent Number: 4,928,541
[45] Date of Patent: May 29, 1990

[54] GROUNDWATER SAMPLING APPARATUS

[75] Inventors: Donald A. Toon, Burlington; Douglas J. Belshaw, Georgetown, both of Canada

[73] Assignee: Solinst Canada Limited, Ontario, Canada

[21] Appl. No.: 305,447

[22] Filed: Feb. 2, 1989

[30] Foreign Application Priority Data

Feb. 5, 1988 [GB] United Kingdom ................ 8802700

[51] Int. Cl.$^5$ .............................................. G01N 1/12
[52] U.S. Cl. .............................. 73/864.63; 73/864.81
[58] Field of Search ............ 73/864.51, 864.62, 864.63, 73/864.64, 864.67, 864.34, 864.35, 864.81, 864.85, 864.86, 864.87, 864.91, 863.83, 863.84

[56] References Cited

U.S. PATENT DOCUMENTS

| | | | |
|---|---|---|---|
| 2,260,419 | 10/1941 | Wrightsman | 73/864.62 |
| 3,892,130 | 7/1975 | Winget et al. | 73/864.62 |
| 3,915,677 | 10/1975 | Oppegaard | 73/864.86 |
| 4,406,171 | 9/1983 | Ueberschaer | 73/864.62 |
| 4,625,574 | 12/1986 | Robbins | 73/864.91 |
| 4,635,487 | 1/1987 | Gowing | 73/864.62 |

FOREIGN PATENT DOCUMENTS

| | | | |
|---|---|---|---|
| 2633333 | 1/1978 | Fed. Rep. of Germany | 73/864.62 |
| 0859855 | 8/1981 | U.S.S.R. | 73/864.34 |

*Primary Examiner*—Robert R. Raevis
*Attorney, Agent, or Firm*—Anthony Asquith & Co.

[57] ABSTRACT

The sampler includes a cylinder, plugged at the lower end, the plug having a first one-way check valve to permit the sample to flow upwards into the chamber. A piston is slidable in the bore, and includes a second one-way check valve, which permits the sample to flow upwards through the piston. In use, the sampler is pressurized from above, in order to hold both valves closed, and lowered to the correct depth; the pressure is released, and the sample flushes through the chamber of the sampler. The sampler is then re-pressurized, and drawn to the surface, with the sample remaining totally contained and maintained at depth-pressure. The sample may be transferred out of the chamber for analysis, by pressurizing the piston, without the sample losing its depth-pressure status.

8 Claims, 4 Drawing Sheets

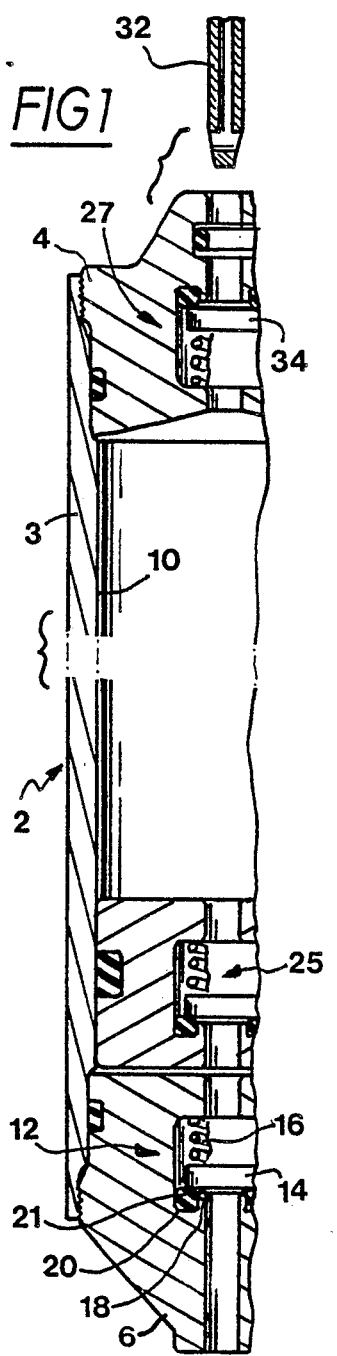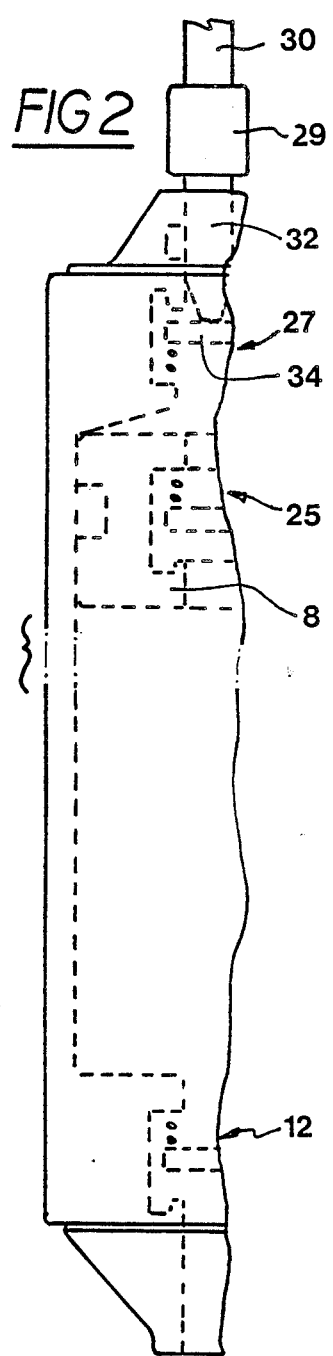

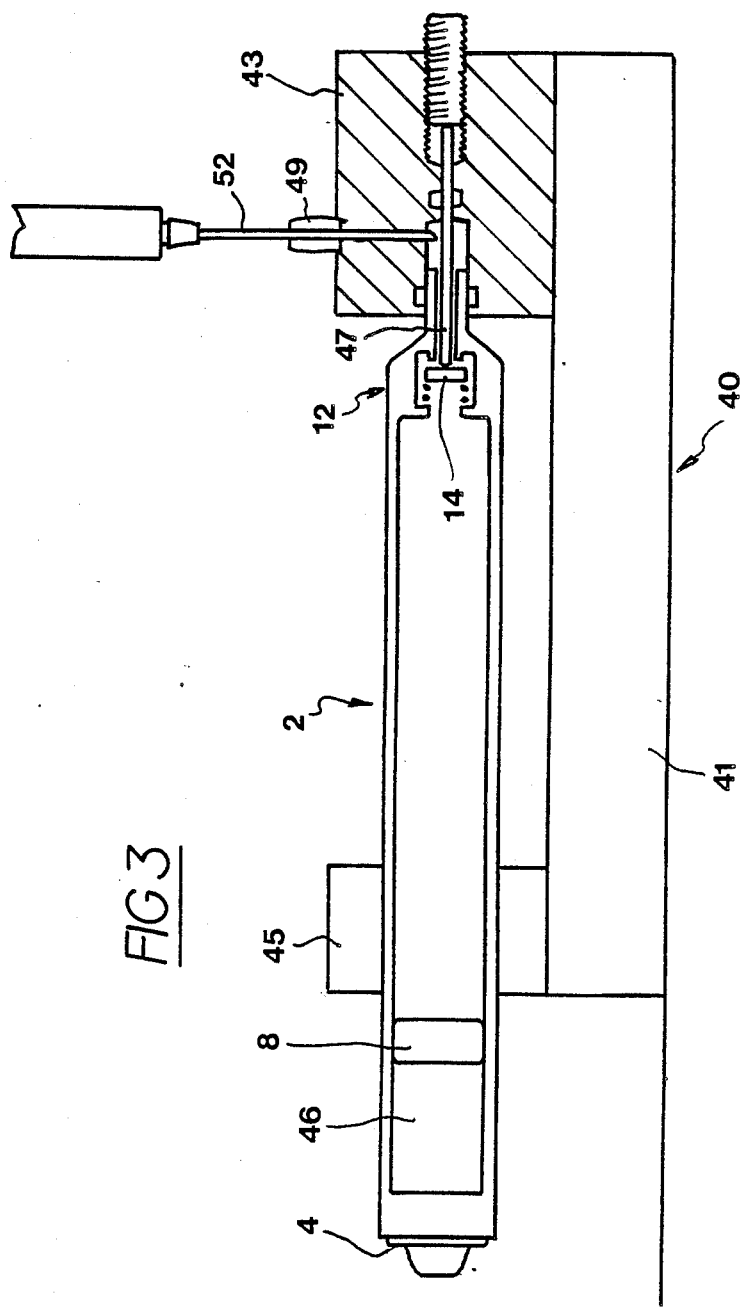

GROUNDWATER SAMPLING APPARATUS

This invention relates to the collection, from a hole in the ground, of a sample of groundwater, and to the transport of the sample from the collection point to the laboratory for analysis.

It is a common to analyse samples of groundwater for the purpose of detecting contaminating substances in the water. The volatile hydrocarbons, such as gasoline, are among the substances which may sometimes be present in groundwater, and which, if present, are required to be detected and quantified. The invention is concerned with making sure that whatever contaminants were present in the water when the water was in the ground are still present when the water comes to be analysed in the laboratory.

GENERAL DESCRIPTION OF THE INVENTION

It is recognized in the invention that one of the sources of error with previous methods of obtaining samples was that, after the sample had been removed from the ground, but before the sample had been analysed, the sample was exposed to the atmosphere.

It is recognized that such exposure led to huge errors in analysis. The volatile contaminants, if present in the water, include a gaseous component, and the bubbles of the gas are entrapped in the liquid water. If the sample is exposed to the atmosphere, many of these bubbles simply expand and burst, and the gas is dissipated into the air, and therefore is not detected.

The physical size of the bubbles is determined by the prevailing pressure in the water, and this pressure is dependent on the depth below the surface. The bubbles of gas or vapour may be entrained or dissolved in the water, and the inter-reaction between the contaminant and the water, including the extent to which such entrainment or solution occurs, depends on the size of the bubble and the depth-pressure of the water.

Another source of error, when the sample was exposed to the atmosphere, was that air was admitted into the container from which the sample was transferred to the analysis apparatus, and this again caused errors when the gaseous content of the sample was measured.

It is recognised in the invention that these errors may be alleviated by (a) maintaining the sample constantly at the pressure the sample was at in the location from which it was drawn (b) containing the sample at all times so that any volatiles present in the sample cannot escape and (c) preventing atmospheric air from entering the sample.

A preferred apparatus for putting the invention into practice comprises a container or sampler having an entry port. The entry port leads to a chamber, and the chamber is of variable volume. The chamber of variable volume includes an exit port.

The entry and exit ports are provided with respective check-valves. The check-valves are so arranged that when the sampler is lowered into the water, the water enters the chamber through the entry port, and flows right through the chamber, and out at the exit port.

The sampler is connected to the surface via a supply line, and pressure is applied through the line to the sampler, in order to close the check-valves and trap the sample within the chamber. The sampler is then raised to the surface, while the pressure is maintained to keep the check-valves closed. Once the sampler has been raised, the pressure is locked in, and the sampler may be stored and transported, as required.

For gas-chromatography, it is usually required that the sample be inserted into a syringe, for injection into the chromatograph. In the invention, the sample (or a portion thereof) is transferred from the sampler to a syringe without losing pressure, and without exposing the sample to air.

In the invention, the sample is extracted from the sampler by applying pressure to the movable wall. Preferably, the sample is ejected through the entry port, the check-valve in the entry port being mechanically held open to allow the sample to emerge.

DETAILED DESCRIPTION OF A PREFERRED EMBODIMENT

By way of further explanation of the invention, an exemplary embodiment of the invention will now be described, with reference to the accompanying drawings, in which:

FIG. 1 is a diagrammatic cross-sectional view of a sampler which embodies the invention;

FIG. 2 is a diagrammatic cross-sectional view of the sampler of FIG. 1, showing the sampler in position in a body of groundwater, during collection of the sample;

FIG. 3 is a diagrammatic cross-sectional view of the sampler of FIG. 1, showing the sampler in position for the operation of transferring the sample of water from the sampler to an analysis apparatus.

Figure 5A:
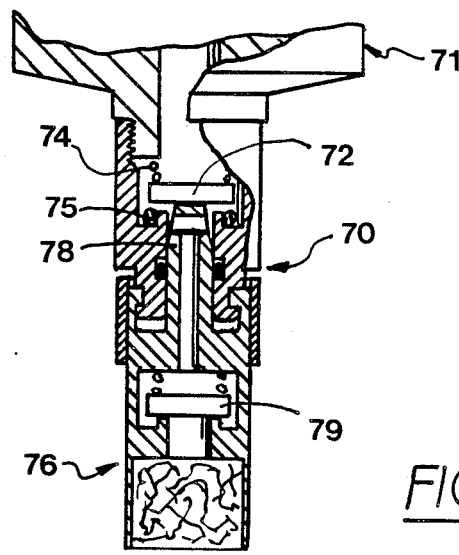
Figure 5B:
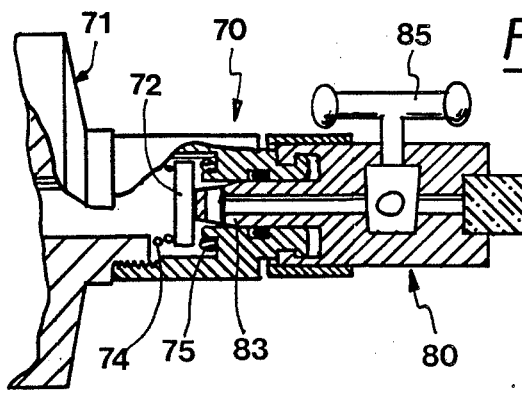

FIGS. 5A and 5B include a diagrammatic cross-sectional view of a portion of a further alternative sampler; FIG. 5A also shows a complementary check-valve and filter assembly, and FIG. 5B also shows a complementary syringe holder.

The sampler 2 shown in FIG. 1 comprises a cylindrical body 3, which is provided with an upper plug 4 and a lower plug 6. A piston 8 is slidable within a bore 10 of the cylinder.

The lower plug 6 is provided with a check-valve 12. The check-valve 12 includes a valve member 14 which is urged by means of a spring 16 onto a valve seat 18. The seat 18 has a recess 20, in which is received an O-ring 21.

The piston 8 is provided with a similar check-valve 25.

The upper plug 4 is provided also with a check-valve 27. The check-valve 27 however is different from the check valves 12 and 25, in that the check-valve 27 forms part of a self-sealing mechanical coupling 29.

The coupling 29 is provided for the purpose also of securing the sampler 2 to a suspension line 30. The suspension line 30 comprises a tube, through which fluids may be conveyed. The coupling 29 includes a probe 32, and when the coupling 29 is assembled, the probe 32 unseats the valve member 34 of the check-valve 27. Once the coupling 29 is assembled, and the probe thereby inserted, it will be noted that the check-valve 27 remains open, irrespective of the pressure differentials operating on the sampler. When the coupling 29 is released, the probe 32 is withdrawn, and the valve member 34 re-seats itself, thus sealing within the sampler whatever fluid is contained therein.

In order to receive a sample of groundwater, the sampler 2 may be operated in the following manner.

First, the tubular suspension line 30 is connected to the sampler 2 by means of the coupling 29. A source of compressed gas, perhaps air but preferably nitrogen, is applied to the remote end of the line 30. The pressure of the gas is of sufficient magnitude to ensure that the valves 12, 25 remain closed.

The sampler is lowered down into the ground-hole, and into the groundwater within the hole. The pressure from the source of compressed gas is enough to keep both check-valves 12, 25 closed as the sampler is lowered into the water.

When the sampler has been lowered to the desired depth, the pressure from the source of compressed gas at the surface is released. The pressure differential across the check-valve 12 now exceeds it cracking pressure. The check-valve 12 therefore opens, allowing groundwater from the hole to flow into the sampler. The incoming water drives the piston 8 upwards, until the piston presses against the upper plug 4. The pressure of the water also exceeds the cracking pressure of the piston check-valve 25, which therefore also opens, allowing the groundwater to flush right through the sampler and into the line 30. The water rises up the line 30 to a level commensurate with the depth of the groundwater in the hole.

It will be noted that when the water has finished flowing into and through the sampler, the sampler is completely filled. It will be noted that the design of the sampler is such that there is no head space below the piston 8 in which air might be trapped, so that the sample contained within the sampler consists only of groundwater, and contains no air brought down from the surface.

The line 30 is now re-pressurized, in order to maintain the pressure inside the sampler. The line 30 is hauled in, and the sampler is retrieved from the hole.

Once the sampler is out of the hole, the coupling 29 is disconnected. The probe 32 is thereby withdrawn from the valve 27, which causes the member 34 of the valve to close, and to seal the contents of the sampler. The sampler may now be transported to the laboratory.

Next, the sampler is made ready for the operation of extracting the sample of groundwater, the operation to be carried out in such a way that substantially no air is added to the sample, and in such a way that the volatile contaminants, if any are present in the sample, are given substantially no opportunity to escape.

The sampler is mounted in a discharge apparatus 40. This apparatus comprises a frame 41, having rests 43, 45 in which the sampler is clamped.

Figure 4:
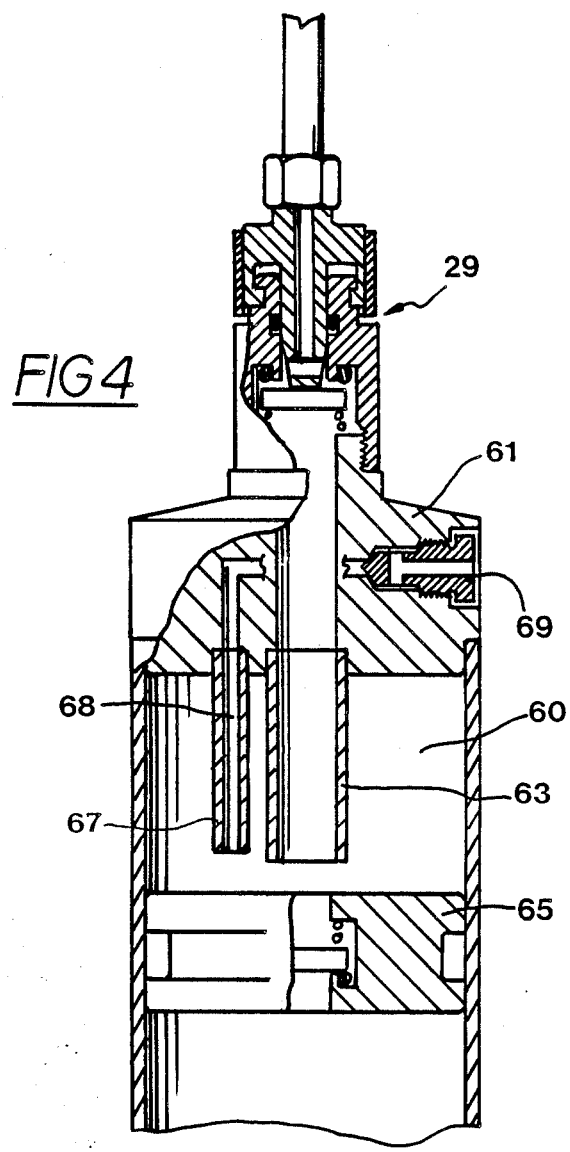
FIG. 4 is a diagrammatic cross-sectional view, corresponding to FIG. 1, of an alternative sampler.

The coupling 29 in the upper plug 4, which is located to the left side in FIG. 4, now is connected to a source of pressurized gas, preferably nitrogen. The gas enters the zone 46 of the sampler to the left of the piston 8, and acts to urge the piston to the right.

The right hand rest 43 is equipped with a plunger 47, which is screw-threaded into the rest 43. The plunger 47 is so arranged that, when the technician screws the plunger towards the sampler, the plunger engages the valve member 14 of the check-valve 12, and mechanically unseats the member 14 and thus opens the valve 12.

The piston 8 is urged to the right, under pressure from the left, as described, thus forcing the sample of groundwater out through the check-valve 12.

The rest 43 is also provided with a receptacle 49 for a sample container, which is in the form of a syringe. It is arranged that the groundwater that emerges from the unseated check-valve 12 can enter the needle 52 of the syringe. The pressure acting on the left of the piston 8 is sufficient to drive the piston of the syringe up the body of the syringe, so that the sample of groundwater enters the syringe. The action of filling the syringe can easily be controlled, to the degree of preciseness required to fill the syringe without bursting it, by means of the screw-action plunger 47.

The syringe is so sized that only a portion of the groundwater within the sampler is drawn off into the syringe. Once the portion has been drawn off, the plunger 47 is withdrawn, thereby closing the check-valve 12. The coupling 29 is disconnected, but the pressure of the gas in the zone 46 to the left of the piston 8 serves to keep the sample of groundwater in the chamber under pressure. The sampler 2 may now be removed from the frame 41 and stored, and of course further portions of that sample may be drawn off, in the future, if required.

The filled syringe is removed from the rest 43, and the water it contains is injected into, for example, a gas chromatography machine for analysis.

It is important to avoid adding air to the water in the sample during the step of transferring the portion of the sample to the syringe. In an alternative arrangement of the discharge apparatus, air trapped in the apparatus in the area of the syringe needle may be led off through a bleed valve. The area may be filled with distilled water, which is discharged through the bleed screw.

In another alternative, a bung of self-sealing elastomeric material is incorporated into the rest. The syringe needle may be driven straight through the bung, and withdrawn without leakage after the syringe has been filled.

In the alternative construction shown in FIG. 4, the zone 60 above the piston is more sophisticated than the simple zone 46 shown in FIG. 3. In FIG. 4, the upper plug 61 is provided with a tubular extension 63. It is arranged that the engagement of the piston 65 against the extension 63 defines the upper limit of the travel of the piston 65.

The upper plug 61 is fitted with another tube 67, which is part of a bleed-off passage 68 formed through the upper plug 61, the passage being closed by a bleed screw 69. When the bleed screw 69 is opened, the passage 68 is open to the surroundings.

The operation of the components in the zone 60 of FIG. 4 is as follows. When the sampler has been raised to the ground surface, the pressure within the line 30 is maintained continuously, as has been explained, at a value commensurate with the pressure head at the depth from which the sample of water was taken. The pressure in the line acts upon the piston 65, and thence upon the sample contained within the chamber below the piston. (It may be expected that, as the piston is pressure-balanced between the pressure of the sample and the pressure in the line 30, that the piston will be slightly clear of the end of the extension 63.)

The bleed screw 69 is now opened, whilst the pressure in the line is maintained. The contents of the zone 60 therefore are expelled, by the maintained pressure, through the bleed screw 69.

When the zone 60 has been emptied of water, and is full of gas (preferably nitrogen, as mentioned), the bleed screw 69 is closed. The line 30 may be disconnected from the sampler at the self-sealing coupling 29, the arrangement being that the act of disconnecting the coupling causes the coupling to seal itself, thereby trapping the nitrogen, under pressure, inside the zone (and incidentally sealing off the end of the line 30). The entry mouth of the bleed-off passage 68, i.e. the lower end of the tube 57, is positioned almost at the bottom of the zone 60, so that most of the volume of the zone can be cleared of water, and filled with nitrogen under pressure.

The nitrogen is contained under pressure within the zone 60; it may be noted that the water has been emptied out of the zone, and the gas placed into the zone, whilst the sample of water within the chamber below the piston 65 has been maintained throughout at the correct pressure.

Another reason why it is important to keep the sample at pressure, while the sample is contained within the sampler, may be explained as follows. When the sample (i.e. a portion of the contents of the chamber of the sampler) is taken out of the sampler for analysis, and transferred into, for example, a gas chromatography machine, the sample is allowed to attain room pressure, at the point of analysis. It may be considered therefore that there is little point in taking elaborate precautions to prevent the pressure of the sample from falling while the sample is contained within the sampler. It is recognised in the invention that it is worthwhile to maintain the sample at high pressure, however, because doing so maintains the homogeneity of the sample.

The sampler as described is of sufficiently large capacity that enough water is contained for several analyses. If the pressure of the sample were allowed to drop, the entrapped gases would bubble out of the liquid water, and would inevitably collect at the uppermost point within the chamber. In that event, the analysis of the sample would depend upon the location within the sampler from which the particular portion of the sample happened to be drawn.

It is recognized that, even though the analysis apparatus and procedure allow the pressure of the sample to fall, nevertheless the correct quantities of molecules would not be present in the as-tested portion of the sample if the pressure of the sample had been allowed to drop during storage within the sampler. When the pressure is maintained, the molecules of all the constituents are retained in their correct proportions.

It is important that the integrity of the sample be unquestionable: for example if the collected sample is to be available for analysis by rival parties as evidence in a legal dispute over responsibility for a spill of contaminants. The integrity of the sample is maintained by keeping the sample at depth-pressure during transport and storage.

It is important that the pressure on the sample should be not maintained, but that the pressure should be reliably and manifestly maintained. The provision of the large reservoir for compressed gas in the zone 60, and the arrangement whereby a large volume of compressed gas may be admitted into that zone to replace the liquid therein, ensures that the pressure in the sample (on the other side of the piston) is reliably maintained.

During transport of the samples back to the laboratory, in a truck or aircraft for example, it is important that the check valves 12, 25 do not bounce open. To maintain a good closure-force on the valve members, even under shock and vibration conditions, again it is advantageous if the body of pressurised gas in the zone 60 be large, as in the arrangement of FIG. 4.

The procedure described in relation to FIG. 3 is just one of a number of procedures that are suitable for transferring the sample into a container such as a syringe. FIGS. 5A and 5B, show another manner in which the sampler may be arranged, for the purpose of enabling the sample of water to be extracted from the sampler without losing its pressure.

In FIGS. 5A and 5B, a second self-sealing coupling 70 is provided on the sampler 71, located at the bottom of the sampler. (The self sealing coupling 70 shown in FIGS. 5A and 5B is a standard item and is shown only diagrammatically.) The coupling includes a valve member 72, which is normally held by a spring 74 against an O-ring 75.

FIG. 5A shows a filter and check valve assembly 76 which includes a probe 78. The probe 78 is so arranged that as the assembly 76 is assembled into the coupling 70 the probe 78 unseats the valve member 72, so that when the filter and check valve assembly 76 is assembled into the coupling 70, the coupling 70 allows a free flow of fluids therethrough.

The assembly 76 includes a check valve 79. When the assembly 76 is coupled to the sampler 71, the check valve 79 serves the same purpose as did the check valve 12 in FIG. 1. The assembly 76 includes a filter, which surrounds the assembly, and prevents the larger particles of dirt from entering the sampler.

The assembly 76 is connected to the sampler prior to the sampler being lowered down the hole. When the sample has been taken, and the sample pulled out of the hole, the assembly is uncoupled, and the sample is trapped inside the sampler due to the action of the self-sealing coupling 70. The spring 74 does not need to be light, as does the spring of the check valve 12 or 79, and thus the spring 74 may be strong enough that there is little risk of the valve member 72 in FIGS. 5A and 5B leaking due to the sampler being knocked during transport of the sampler to the laboratory.

In order to extract the sample (or, more usually, a portion of the sample) the sampler 71 is coupled to a syringe holder 80, as shown in FIG. 5B. The holder 80 includes a probe 83 which serves, again, to unseat the valve member 72 as the holder is assembled into the coupling 70. The holder includes a suitable tap 85, which is set to the closed position during coupling. When coupling is complete, the tap 85 may be opened, and the sample will flow into the holder as a result of the pressure that is being maintained in the zone above the piston 8. (NB: the sampler can be in any suitable orientation during extraction of the sample, e.g. upside down, or horizontal.)

The holder 80 includes a bung, which is suitable for receiving the needle of a syringe, for drawing off the sample, once the tap is opened. By carefully controlling the opening of the tap, the technician may control the filling of the syringe by controlling the zone pressure.

It will be noted that the sample will normally fall virtually to atmospheric pressure upon entering the syringe, and it might therefore be supposed that all the precautions taken, as described, to maintain the pressure in the sample have in the end proved superfluous. However, the main reason for maintaining the pressure up to entry of the sample into the syringe has been to maintain the homogeneity of the sample within the sampler, in order to prevent the gaseous components of the sample, if any are present, from separating out of the water. Mere containment of the sample is not sufficient, while the sample is contained within the sampler.

When the sample is finally to be analysed, however, mere containment of the sample is now adequate, because the analysis process basically involves simply counting the various molecules present.

There are other ways of transferring the sample from the sampler to the analysis apparatus: it is contemplated, for example, that the sample may be transferred directly, rather than via the syringe. It is important that no air be allowed into the sample during the transfer process, but it is easy enough to design the holder so that air pockets are eliminated.

We claim:

1. Apparatus for collecting a sample of fluid, and for containing the collected sample, wherein:
   the apparatus includes a chamber, and the chamber is defined by a fixed wall and a movable wall, and the chamber is of variable volume in that the movable wall is movable with respect to the fixed wall;
   the apparatus includes first and second one-way check-valves, each check-valve being arranged so as to permit fluid to flow through itself in one direction only;
   one of the check valves is located in the fixed wall, and the other of the check valves is located in the movable wall;
   the first check valve is so arranged as to permit fluid to flow into the chamber only;
   the second check valve is so arranged as to permit fluid to flow out of the chamber only;
   the apparatus includes a supply line, which is in fluid-flow communication with the chamber via the second check valve;
   the arrangement of the apparatus is such that, when the pressure in the chamber exceeds the pressure in the supply line, the second check valve is open, and fluid can flow from the chamber into the supply line;
   and the arrangement of the apparatus is such that, when the pressure in the supply line exceeds the pressure in the chamber, the second check valve is closed, and excess of pressure in the supply line acts upon the movable wall in the direction to reduce the volume of the chamber.

2. Apparatus for collecting a sample of fluid, wherein:
   the apparatus includes a cylinder, and a piston which is sealingly slidable within a bore of the cylinder;
   the apparatus includes a lower plug, which is arranged to close off one end of the bore;
   the piston and the lower plug are so arranged as to define between them in the bore a chamber of variable volume;
   the lower plug includes a first one-way check valve, which is so adapted and arranged as to permit fluid-flow through the valve and into the chamber, and to prevent fluid-flow through the valve and out of the chamber;
   the apparatus includes a zone, which comprises that portion of the said bore on the other side of the piston from the said chamber;
   the piston includes a second one-way check valve, which is so adapted and arranged as to permit fluid-flow through the valve from the chamber to the said zone of the bore on the remote side of the piston from the chamber, and to prevent fluid-flow from the zone into the chamber;
   the apparatus includes a supply line, which is in fluid flow communication with the said zone and with a station that is remote from the zone, whereby pressure may be applied to the said zone from the remote station;
   and the arrangement of the apparatus is such that, when the pressure in the supply line exceeds the pressure in the chamber, the second check valve is closed, and the excess of pressure in the supply line acts upon the piston in the direction to reduce the volume of the chamber.

3. Apparatus of claim 2, wherein the cracking pressure setting of the second check valve is of a magnitude greater than the pressure required to overcome frictional resistance, and to cause the piston to move along the bore.

4. Apparatus of claim 3, wherein the cracking pressure setting of the first check valve is less than the cracking pressure setting of the second check valve.

5. Apparatus of claim 2, wherein:
   the zone is provided with an openable bleed-off passage, which is normally closed and fluid-tight, but through which, when opened, fluid under pressure in the zone can be expelled from the zone;
   and the bleed-off passage has an entry mouth, and the location of the entry mouth is such that a substantial volume of the zone lies above the entry mouth, when the apparatus is in the orientation wherein the zone is above the chamber.

6. Apparatus of claim 2, wherein the apparatus includes an upper self-sealing coupling, by means of which the supply line may be disconnected from the zone, and by means of which, when the supply line is disconnected, fluid pressure may be contained within the zone.

7. Procedure for obtaining a sample of fluid, and for presenting the sample for analysis, comprising the steps of:
   providing the apparatus of claim 2;
   noting the depth-pressure of the sample, being the pressure of the fluid at the depth at which the sample is to be obtained;
   at the remote station, applying a greater pressure than the depth-pressure to the supply line, and thereby to the zone; placing the apparatus to the said depth;
   at the remote station, releasing the pressure in the supply line, and thereby in the zone, whereby the piston moves in the sense to increase the volume of the chamber, and whereby the first check valve opens, and permits the sample to flow into the chamber;
   allowing time for the sample to flush through the chamber and into the zone;
   then, at the remote station, applying a greater pressure than the depth pressure to the supply line, and thereby to the zone, whereby the second check valve closes, and the piston moves in the sense to decrease the volume of the chamber, whereby the first check valve closes;
   recovering the apparatus from the depth, whilst still maintaining the said greater pressure in the zone;
   and transporting at least that portion of the apparatus which contains the sample to an analysis station, whilst still maintaining the said greater pressure in the zone.

8. Procedure of claim 7, including the further steps:
   of connecting the apparatus to a discharge apparatus;
   of establishing a passage between the chamber and the discharge apparatus;
   and of maintaining pressure within the zone, both during and after the establishment of the said passage, whereby the piston moves to reduce the volume of the chamber, thereby to urge the sample through the passage and into the discharge apparatus.

* * * * *